US00PP13562P2

(12) United States Plant Patent
Asai

(10) Patent No.: US PP13,562 P2
(45) Date of Patent: Feb. 18, 2003

(54) DENDROBIUM PLANT NAMED STARDUST 'FIREBIRD'

(76) Inventor: Nobuyuki Asai, 60 Aza Hanto, Oaza Ishihama, Higashi Uramachi, Chita Gun, Aichi-ken (JP)

( * ) Notice: Subject to any disclaimer, the term of this patent is extended or adjusted under 35 U.S.C. 154(b) by 0 days.

(21) Appl. No.: 09/542,140

(22) Filed: Apr. 4, 2000

(51) Int. Cl.[7] ..... A01H 5/00

(52) U.S. Cl. ..... Plt./311

(58) Field of Search ..... Plt./311

(56) References Cited

PUBLICATIONS

GTITM UPOVROM Citation for 'Stardust Firebird' as per JP PBR 11311; Oct. 9, 1998.*

* cited by examiner

*Primary Examiner*—Kent L. Bell
(74) *Attorney, Agent, or Firm*—Townsend and Townsend and Crew LLP

(57) ABSTRACT

A new and distinct variety of Dendrobium Plant named Stardust 'Firebird', is particularly characterized by its pure bright orange sepal and petal color and lip with bright yellow-orange and dark orange red checkered pattern, its economical propagation via tissue culture, its spring bloom and its small plant size which makes it suitable for packaging and shipment.

2 Drawing Sheets

DESCRIPTION

This invention comprises a new and distinct variety of Orchid named Dendrobium Stardust 'Firebird', a hybrid of the Genus Dendrobium (*Dendrobium unicom×Dendrobium ukon*), referred to herein by its grex and varietal name Stardust 'Firebird'. Stardust 'Firebird' is a distinct variety selected from progeny of a cross between the unpatented *Dendrobium unicum* and *Dendrobium unkon*. The same cross has produced other Stardust family members (see below).

The chronology of events leading to selection of Stardust 'Firebird' is as follows: *Dendrobium unicum* and *Dendrobium unkon* were crossed in 1980 and seedlings were placed in flasks in October of that year. These seedlings were grown to maturity, flowered, and the Grex epithet Stardust was registered with The Royal Horticultural Society, The International Registration Authority for Orchid Hybrids, in 1986 by N. Ashi. From this group of seedlings a plant with desirable characteristics (i.e., good flowers, compact growth habit, and fast growth), was selected and given the varietal epithet 'Firebird'.

This plant was then reproduced asexually using conventional meristem culture techniques for tissue culture of orchids (*Plants from Test Tubes*, Lydiane Kyte and John Kleyn, eds., Timber Press (1996)). Asexual reproduction took place at 60 Aza Hanto, Oaza Ishihama, Higashiuratnachi, Chita Gun, Aichi, Japan, and Stardust 'Firebird' reliably reproduced true to type. A long testing period followed.

In February of 1993, the plants of Stardust 'Firebird' continued to display the desirable characteristics selected for. These plants were then examined for their susceptibility or immunity from known diseases, namely, Dendrobium virus, Dendrobium Thabdo virus and Tomato Spotted Wilt virus. Stardust 'Firebird' displayed immunity to those diseases. All developmental work was done in a glass greenhouse located at Aichi-ken, Japan where minimum temperature was kept at 13° C.

Stardust 'Firebird' is descended from 5 species of the genus Dendrobium. These are *Dendrobium unicum, Dendrobium moniliforme, Dendrobium aureum, Dendrobium signatum,* and *Dendrobium nobile*. These species have been extensively used in hybridizing and are found over an extremely large area having a wide range of habitat elevations. The habitat area extends from India in the West to Japan in the north, and Australia and New Zealand in the south. Eastward, the habitat includes most of the Pacific Islands. The species are found from sea level to elevations as high as 12,000 feet. It is impossible to make accurate generalizations about the horticulture of the Dendrobium species but it can be said that its hybrids have cultural requirements which are similar to parents *Dendrobium unicum* and *Dendrobium ukon*, neither which is patented, and form a predictable guide. *Dendrobium unicum* and *Dendrobium ukon* and Stardust 'Firebird' have rather large attractive flowers and are generally easy to cultivate.

*Dendrobium unicum* is a very distinctive species from Thailand and Laos. It has a deep orange color. It differs significantly from Stardust 'Firebird' in that the petals and sepals are very narrow and strongly reflexed, the lip is larger than petals and sepals, is brownish orange and has a 3 ridged callus along the center. *Dendrobium ukon* is a hybrid, registered with The Royal Horticultural Society in 1979 by H. Furuse. It differs from Stardust 'Firebird' in growth habit, in the pseudobulbs being quite large and swollen in the middle, and in flower shape and size. Flowers are usually white or pink, petals larger than sepals, with a broad flat lip. Petals and sepals are also much wider at the apex than at the base.

IN THE DRAWINGS

SPECIFIC DESCRIPTION

Figure 1:
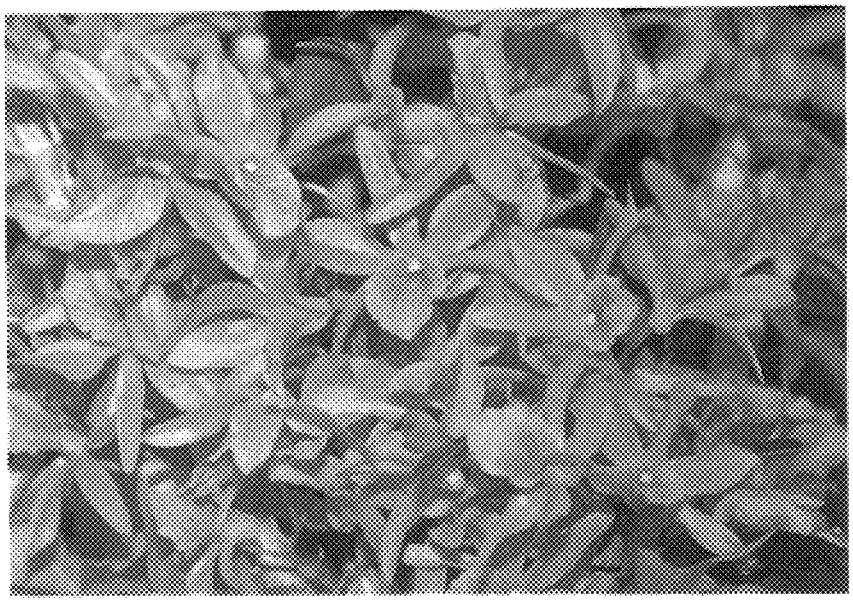
FIG. 1 is a close up view of the inflorescence of Stardust 'Firebird'.
Figure 2:
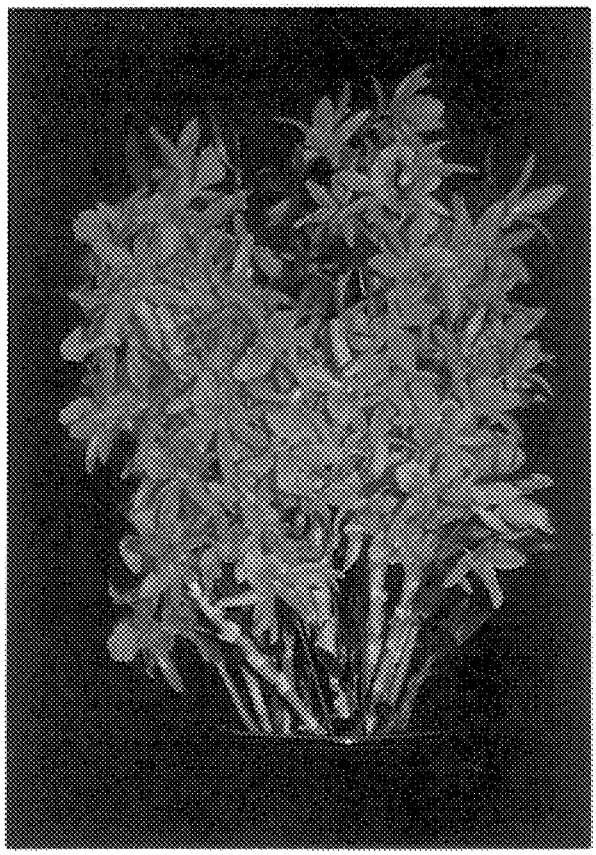
FIG. 2 is a side view of the flowers on the stalks of Stardust 'Firebird'.
Figure 3:
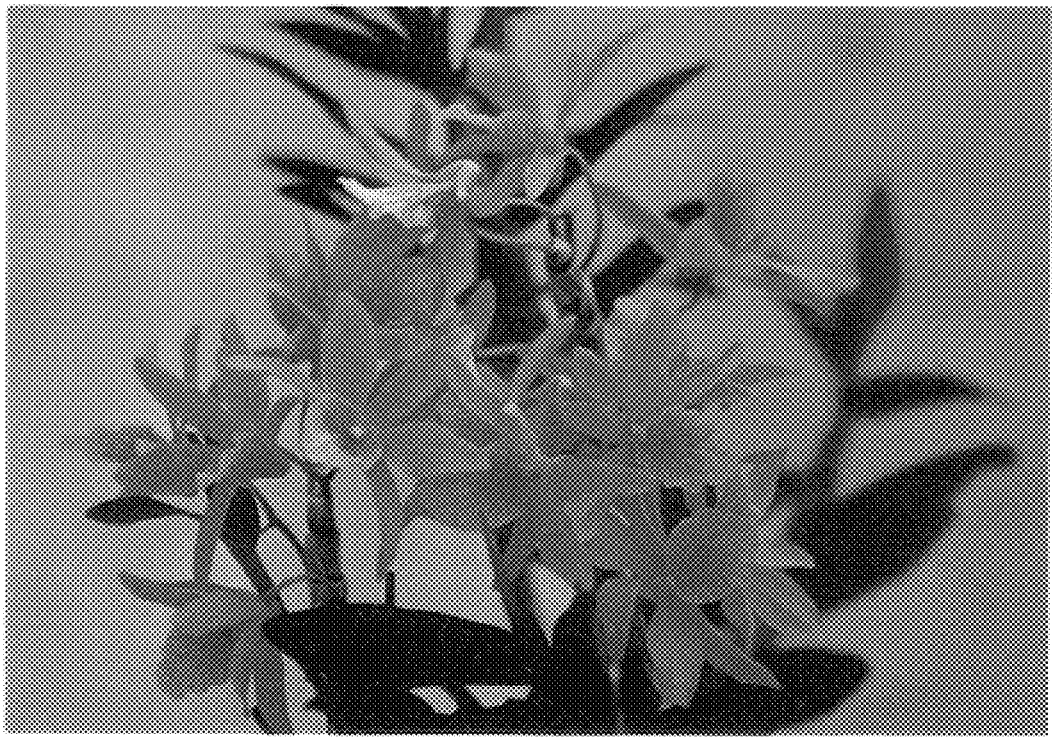
FIG. 3 is a side view of a potted plant showing the flowers, stalks and leaves of Stardust 'Firebird'.

All color references are to the Japanese Horticultural Society Color Chart and the Pantone color chart. Colors are approximate as they depend upon horticultural practices such as exposure to light and fertilization, among others, but without any change in genotype.

The following observations describe the characteristics of Stardust 'Firebird' under greenhouse conditions in Aichi-ken, Japan, when 1½ years old and grown in a pot size 4½ inches in diameter and 4¾ inches in depth which conditions closely approximate those used in actual growing practice:

The characteristics which distinguish Stardust 'Firebird' from the closest similar commercial variety, Stardust 'Chiyomi', (unpatented), have been observed repeatedly, namely, the lateral sepals turn opposite those of Stardust 'Chiyomi' and the dark orange red-checkered pattern of the Stardust 'Firebird' flowers is significantly different from the color pattern of Stardust 'Chiyomi'.

PLANTS

Potted plants of Stardust 'Firebird' grow very quickly, producing marketable flowering plants in spring. The flowers have no fragrance. It takes 12 to 14 months to produce a flowering plant from a rooted cutting. The typical and observed plant height from soil level to top of the flowers is 15 inches and the width is 7 inches.

INFLORESCENCE

The color of the flowers (sepals and petals) produced by Stardust 'Firebird' are a pure bright orange color (Japanese Horticultural Society Color Chart No. 1305). The color designations are the same for both surfaces of the sepals, petals, and lip base. The lip base color is bright yellow-orange (JHS Color Chart No. 1906) and has a dark-orange red checkered pattern (JHS Color Chart No. 0714). The color of the entire lip is the same as that of the lip base.

The size and shape of the flowers produced by Stardust 'Firebird' are short, upward in angle and are in a folding-inverted pattern. Flower diameter is 2¾ inches and depth is 1½ inches. There are three sepals, one dorsal and two lateral. The front view of the dorsal sepal is linear and obtuse in shape. The front view of the lateral sepals is stretched kidney shape. The dorsal and lateral sepals are similar in size. The apex and base are obtuse, margin is entire, and width is the same from apex to base. There are two petals which are similar in size and shape. The front view of the petals are stretched and lozenge-shaped. Apex and base are obtuse, margin entire, and spatulate. There is one lip, margin entire, slightly undulated. The lip apex is acute, base obtuse, and the front view is bell-shaped. The lip with base surrounds the column. Flowers are produced at the top and middle areas of the pseudobulb at the nodes opposite the leaves on short pedicels in clusters of two or three. There are 20 to 24 blooms per pseudobulb. The natural flowering season is in March and the blooms last on the plants for six to eight weeks. The flower is simple, having both male and female reproductive organs in the same flower.

RACEME

The raceme is medium in size and in upright position. Each raceme contains two or three flowers borne on short pedicles. The raceme is ¾ to 1 inch in length, 3/16 inch in width. The color is JHS 3514.

LEAF

The overall shape of a leaf blade is long and elliptic to ovate with an uneven obtuse apex which faces horizontally. A cross section of leaf is shaped almost flat and faces upward. There are seven to ten leaves on each pseudobulb. Margin is entire. Foliage is ¼ inch wide and 3¼ inch long. Upper surface color is Pantone 582C and the undersurface color is Pantone 583C. Leaves are sessile.

PSEUDOBULB

The front view of a pseudobulb of Stardust 'Firebird' is linear and the cross section is rounded fan shape. Its height is 12 inches to 15 inches. Its diameter is ⅜ inches and its color is JHS 2907.

REPRODUCTIVE ORGANS

Column—one, 6 mm×8 mm, tip color—JHS 3304. Pollinia—four, 0.3 mm ×1 mm, color JHS 2902. Ovary—one, 4 mm×9 mm, color JHS 2866.

PROPAGATION

Stardust 'Firebird' may be propagated from off-shoots which frequently arise from the lower bracts of the inflorescence. The resulting plants are detached from the mother plant and may be planted in a suitable substrate. Propagation may also be accomplished via in vitro tissure culture using standard orchid micropropagation techniques. Stardust 'Firebird' is a single genotype.

DISEASE

In January, 1994, Stardust 'Firebird' was examined for Dendrobium virus, Dendrobium Thabdo virus and Tomato Spotted Wilt virus. All plants of Stardust 'Firebird' appeared negative to all three diseases. The disease-free plants were isolated from other plants for propagation. Thus far, plants of Stardust 'Firebird' continue to display immunity from all three diseases.

I claim:

1. A new and distinct variety of Dendrobium plant named Stardust 'Firebird' having the characteristics herein illustrated and described.

* * * * *